United States Patent [19]
Thompson

[11] Patent Number: 5,165,893
[45] Date of Patent: Nov. 24, 1992

[54] METHOD AND DEVICE FOR FILLING AND SEALING ROOT CANALS OF TEETH

[76] Inventor: Ronald A. Thompson, 1911 Elm St., Manchester, N.H. 03104

[21] Appl. No.: 869,895

[22] Filed: Apr. 15, 1992

Related U.S. Application Data

[63] Continuation of Ser. No. 708,874, May 31, 1991, abandoned.

[51] Int. Cl.$^5$ .............................................. A61C 5/02
[52] U.S. Cl. .................................... 433/224; 433/81
[58] Field of Search ................................ 433/81, 224

[56] References Cited

U.S. PATENT DOCUMENTS

| | | | |
|---|---|---|---|
| 1,649,508 | 11/1927 | Carmichael | 433/224 |
| 4,565,722 | 1/1986 | Highgate et al. | 433/224 |
| 4,758,156 | 7/1988 | Johnson | 433/81 |

Primary Examiner—John J. Wilson
Attorney, Agent, or Firm—Allegretti & Witcoff, Ltd.

[57] ABSTRACT

A device for filling and sealing root canals of teeth is disclosed. The device comprises an adaptable liner having a coating of a root canal sealer or bonding material on its external surface which seals the root canal when the liner is expanded or inflated.

22 Claims, 2 Drawing Sheets 5,165,893

METHOD AND DEVICE FOR FILLING AND SEALING ROOT CANALS OF TEETH

BACKGROUND OF THE INVENTION

This application is a continuation of Ser. No. 07/708,874 filed May 31, 1991 now abandoned.

The present invention relates to a new method for the treatment of root canals of teeth. The invention includes within its scope a novel device for hermetically sealing root canals.

Endodontic therapy or root canal therapy has been practiced for over a hundred years. Present methods of root canal therapy were developed as an extension of the principles conceived to remove tooth decay and fill cavities. According to present methods, root canal therapy involves cleaning of all infected and diseased tissue and their by-products from the root system, shaping the root canal to facilitate filling and insertion of filling material to obliterate the space formerly occupied by the root canal tissue. There exists a variety of methods for root canal therapy as described below.

A basic method involves a single filling cone which is inserted into a root canal to obturate the canal. Initially, a reamer of the same dimension as the filling cone is used to shape the canal. After this preparation, the filling cone is inserted and cemented into place within the root canal.

Lateral condensation is a method in which several filling cones, a primary cone and auxiliary cones, are inserted into a root canal. The primary cone is inserted and cemented to the seat of the root canal. Using a tapered spreader, the primary cone is then squeezed against the side of the root canal and a second cone is inserted and cemented into place. This process is continued until the root canal is completely obturated which can require up to 10 to 15 filling cones.

Vertical condensation of warm or hot gutta percha is yet another method of sealing root canals. After cementing a primary cone short of the apex of the root canal, heat application is alternated with a series of smaller and smaller pluggers until the gutta percha is moved to the apex. This is often possible when the smallest plugger approaches the apex of the tooth within 3 to 5 millimeters. The space is then backfilled. Lateral canals are packed and sealed as a consequence of lateral expansion of a wave of heated gutta percha. Alternatively, small segments of gutta percha can be used in this method which are inserted into the root canal, heated in order they can adhere to one another and each backfilled one at a time until the root canal is filled.

All three of these methods, the single filling cone, lateral condensation and vertical condensation apply root canal cement or sealer around the individual cones or in between segments as a binding agent.

Another method employs an injection gun which injects warm or hot gutta percha into a root canal. The injector initially places heated gutta percha at the seat of the root canal which is then condensed with a plugger into the root tip. The injector then backfills the root canal by injecting additional gutta percha into the root canal until it is obturated.

A similar method involves heating gutta percha on a flexible metal carrier used to insert the gutta percha into the root canal.

The objective of these methods is to produce a solid, homogenous filling which completely seals a root canal and its associated lateral canals. However, this result is difficult to achieve. What is produced is an inert, passive plug within the root canal. It does not provide reinforcement to the tooth, allowing the tooth to be susceptible to fracture, nor does it always provide a desirable seal.

In addition, using instruments to plug or condense filling material, as is the case with many of the methods described, there is a risk the tooth will be fractured as the plugger spreader comes into contact with the walls of the tooth. Inserting pluggers within the desired 3 to 5 millimeters of the root tip is the most difficult task to accomplish. Attempting to pack the filler material tightly into the root tip with a plugger can result in longitudinal root fractures.

Among the problems associated with the treatment methods utilizing gutta percha, perhaps the most common problem is the volumetric shrinking or contraction of gutta percha as it cools within the root canal. Cooling gutta percha contracts after application and can pull away from the root canal wall, creating spaces between the canal wall and the gutta percha. As a result, reinfection and inflammation of periapical tissues can occur.

In addition, the problem of overextension can arise due to the application of excessive amounts of gutta percha to a root canal. It is particularly difficult to determine the correct amount of gutta percha to apply to a root canal. If too much gutta percha is applied, gross overextension of filling material occurs as it is forced out of the root canal into the periapical tissues surrounding the tooth. This is not desirable.

Another problem associated with gutta percha is attempting to seal canals of different diameters in the same tooth with gutta percha of the same temperature and viscosity. For example, it is easier to fill wider canals than it is to fill the tiny narrow lateral canals with gutta percha. Greater pressure is required to fill the smaller canals and overextension can result.

Lateral condensation and vertical condensation of warm or hot gutta percha are very time consuming methods. Patients typically endure long, tiring gutta percha packing and condensing sessions. This is especially important to those with temporomandibular joint disease and to those with advanced cardiovascular disease.

DESCRIPTION OF PRIOR ART

Many endodontic methods use polymeric compounds to obturate the root canal of a tooth. Such compounds are typically plugged, packed or injected into root canals. U.S. Pat. No. 4,813,876 discloses certain biocompatible, polymerizable compositions which can be used in direct contact with living tissue and are useful as endodontic filling materials. U.S. Pat. No. 4,565,722 discloses a shaped polymeric composition which is suitable for dental use and is capable of absorbing liquid, and upon absorbing liquid expands in one direction, i.e. laterally in the case of a dental insert. U.S. Pat. No. 4,362,508 describes a method and apparatus for producing a core to fill a prepared root canal whereby gasifiable impression material is injected into the root canal to create a cast replicating the root canal from which the core is produced.

For further description of endodontic methods and systems for obturating root canal systems, see Chapter 8 entitled "Obturation of the Root Canal System" by Nguyen, N.T. in *Pathways of the Pulp*, (Stephen Cohen and Richard C. Burns, Eds., Fifth Edition), Mosby-Year Book, Inc. St. Louis, 1991.

SUMMARY OF THE INVENTION

A principal object of the present invention is to provide a new method for filling and sealing root canals which is easier than the present endodontic techniques, and avoids common problems associated with those techniques. Another object of the present invention is to provide a device for the practice of this new method.

Broadly speaking, the invention provides for a device which is suitable for applying root canal sealer or bonding material to the dentin surface of a primary root canal and filling associated lateral canals with sealer or bonding material, while concomitantly acting as a liner for the root canal cavity and hermetically sealing the primary and lateral canals. The device comprises, in combination, 1. a liner of adaptable material, for example non-rigid, flexible, expandable material, which can be readily expanded or inflated and shaped to conform to the contours of the dentin surface of the primary root canal, having a coating of root canal sealer or bonding material on its external surface, and 2. a means of inserting the device into the root canal and 3. a means of expanding or inflating the liner.

The device is inserted into a root canal by a means of insertion after the root canal has been appropriately prepared for endodontic treatment. Upon cementing the device to the seat of the canal, the liner element of the device readily expands or inflates like a balloon in response to positive pressure created within the liner.

The positive pressure forces the external surface of the liner into intimate contact with the dentin surface of the primary root canal. The liner molds or conforms under this pressure to the shape and irregularities of the dentin surface. The root canal sealer or bonding material coating the external surface of the liner is simultaneously applied throughout the entire dentin by the force of expansion or inflation. The result is a thorough application of root canal sealer or bonding material to the dentin of the root canal system, hermetically sealing the primary canal and its associated lateral canals.

Depending upon the condition and anatomy of the root canal system being treated, the liner can be left in place to form a continuous lining of the root canal cavity or it can be removed from the root canal entirely after the sealer or bonding material has set or cured.

Similarly, as conditions may dictate, the means for inserting the device into the root canal can be removed or left in place. In the first instance, removing the means of insertion produces a void or vault in the liner which is then filled with materials typically used to obturate root canals. If the means of insertion is left in place, it can act as a reinforcing core or root canal filler to strengthen the tooth.

DETAILED DESCRIPTION OF INVENTION

Figure 1:
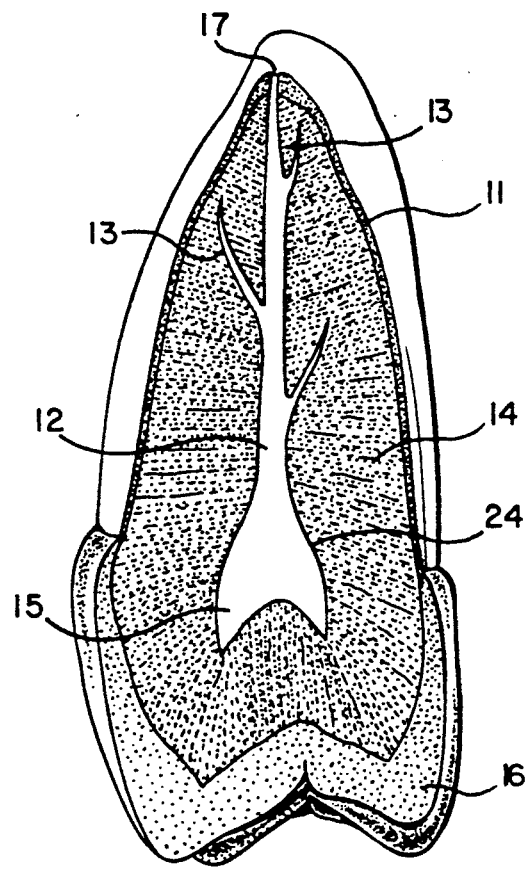

The invention is described in greater detail below with references to the accompanying drawing in which FIG. 1 is a distal view of a general anatomy of a tooth.

Figure 2:
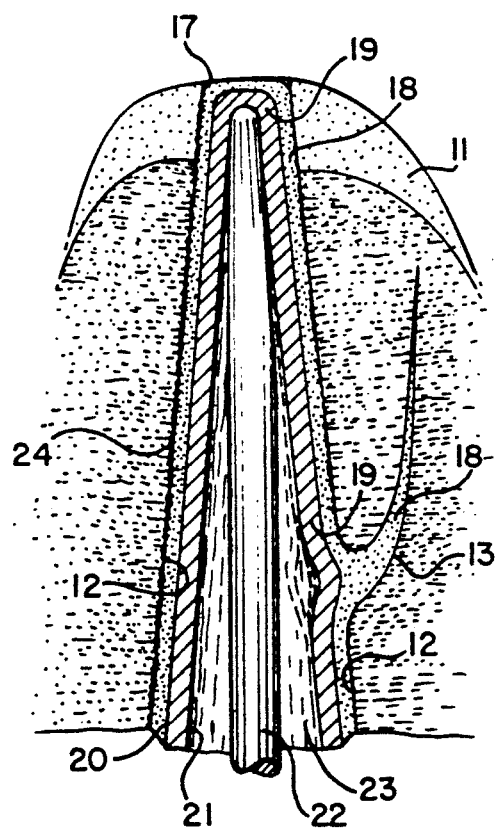

FIG. 2 shows a sectional view of a typical device according to this invention.

Referring to FIG. 1, the tooth comprises an outer layer of cementum (11), a primary root canal (12), and associated lateral canals (13), surrounded by dentin (14). The dentin surface is also referred to as the wall of the root canal cavity or wall of the primary root canal and indicated by (24). The pulp tissue is generally indicated by reference (15) and the enamel of the tooth is indicated as (16). The apex of the root canal is indicated as (17).

According to the present invention, a basic form of the device as illustrated in FIG. 2 comprises, in combination, a liner (19) constructed of adaptable material which is coated with root canal sealer or bonding material (18) on its external surface (20). The liner is inserted into an appropriately prepared root canal and carried to the apical seat of the canal (17) by a suitable means of insertion or a substrate (22) which may be a conventional plugger, carrier, spreader or a fiber optic plugger, carrier, spreader. The liner is then cemented to the apical seat of the root canal. Upon removing the substrate (22), a void or vault (23) is created or widened which can be filled with materials appropriate for obturating root canals. The compression of such filling material(s) into the vault (23) by means of the plugger or spreader creates the positive pressure needed to expand or inflate the liner (19). Expansion or inflation of the liner (19) can also be achieved by injection of filling materials into the vault (23) as well.

As the liner (19) expands or inflates in response to this pressure, it conforms to the shape and irregularities of the primary root canal wall (24) as it is pressed against the canal wall. The external surface of the liner (20) and the canal wall (24) form an intimate and continuous interface. The root canal sealer or bonding material (18) which coats the external surface of the liner is forcibly applied by the expanding or inflating liner to the primary root canal wall (24), out through the tiny lateral canals (13) and through the dentin (14) and cementum (11) to the periodontal ligament of the tooth. As the root canal sealer or bonding material (18) is forced out through the lateral canals (13), any remaining pulp tissue is simultaneously forced from these tiny canals and replaced by the sealer or bonding material (18).

The result is the application of a layer of root canal sealer or bonding material (18) to the wall of the primary root canal (24) and the obturation of the associated lateral canals (13) with sealer or bonding material (18). Upon setting or curing the sealer or bonding material, a continuous seal is achieved, hermetically sealing the primary (12) and lateral root canals (13).

A significant advantage is provided by the present invention as compared to prior art systems and methods in that the root canal sealer or bonding material (18) is forcibly applied from within the root canal cavity to the primary canal wall (24) and out through the lateral canals (13) by expansion whereas conventional methods apply sealing and bonding materials to the root canal system by compression as plugging, packing or injecting such materials from outside the tooth into the root canal cavity. With conventional compressions methods, it is difficult to achieve a thorough application of sealer or bonding material since all root canals have curvature. Some root canals have severe curvature at many positions of the root. It is difficult to apply sealing or filling materials to these curvatures by plugging, packing or injection techniques.

Even if a thorough application of sealer or bonding material is achieved, spaces can develop within root canals should shrinkage of sealing or bonding material occur or should it pull away from the canal walls after setting or curing. The present invention has the advantage of applying and maintaining positive pressure from within the root canal cavity to ensure continuous contact between sealing or bonding materials and root canal walls at least until such material have set or cured.

In addition, it is often not possible to mechanically clean the tiny lateral canals associated with a primary canal due to their size. The application by pressure of sealer or bonding material to these lateral canals evacuates pulp tissue which otherwise cannot be removed from the canals and replaces it with sealer or bonding material.

The invention also relates to several modifications of the basic form of the device, as described. Each modification can employ different materials, modes of insertion and modes of expansion or inflation. The anatomy, physical condition and particular circumstances relating to the treatment of a given root canal determine the choice of modification. Such flexibility ensures that the best modification will be applied to effectively obturate a root canal. However, all modifications retain the distinct features of the basic form which characterize the device as novel.

The liner element (19) of the device can be modified by the materials of construction used and the size and shapes formulated. The basic liner is constructed of non-rigid, flexible, expandable material, either man-made or naturally occurring, having at least one or more of the following physical characteristics: porous or semiporous, permeable or semipermeable, contiguous or noncontiguous, nonporous or nonpermeable such as catgut, nylon, polyurethane, polyethylene, PTFE sheets available commercially as Teflon TM or Gortex TM , silicone elastomer, foamable polymer, metallic foil, e.g. tin, gold, silver and the like. This adaptable material must be biologically compatible and appropriate for dental use. It is desirable that the selected material have a low friction surface and sufficient stiffness to facilitate insertion into the root canal. The material, however, must be able to expand or inflate both axially and radially within the root canal in response to the creation of positive pressure within the liner. Because the material is flexible, it can be adapted or molded to conform to the shape and irregularities of the root canal wall.

In its basic form, the liner element (19) is formulated into a shape which is comparable to the shape of the root canal cavity to be sealed and filled. A comparable shape ensures that the liner will completely cover the wall of the root canal cavity as it is forcibly molded by pressure and conforms to the contours of the root canal wall. A shape similar to that of the root canal will allow the liner to achieve a good fit and ultimately a good seal. For example, a cone-shaped liner resembles the shape of the average root canal of an adult tooth in which the root canal tapers from the top of the tooth as it descends toward the root tip or the seat of the canal.

The size of the liner, as is the shape of the liner, is determined by the dimensions of the root canal to be treated. In general, when the liner is initially inserted into the root canal it will be smaller in terms of its overall dimension. However, upon creation of pressure within the liner, it will expand or inflate axially and radially and become "oversized" in relation to the root canal. This is necessary in order to force the liner into intimate contact with the wall of the root canal, and to force the root canal sealer or bonding material throughout the dentin of the root canal.

The means of inserting the device into the root canal or a substrate (22) can be a plugger, carrier, spreader or a fiber optic plugger, carrier or spreader which places the liner at the apical seat of the root canal. In its basic form, the substrate can be removed from the liner entirely or left in place upon insertion. The substrate chosen is dependent upon the particular circumstances and physical anatomy and condition of the root canal to be treated. The choices are varied, allowing the best means to be used for a given clinical condition.

For example, the plugger or carrier can be fiber optic if a light curing bonding material is compressed into the vault to fill and expand the liner. The fiber optic plugger or carrier would insert the liner into the root canal and also cure the composite material once applied. After curing, the plugger or carrier can be removed or left in place within the root canal. When left in place, the plugger or carrier acts as a reinforcing core which is bonded to the composite material. The composite material and plugger or carrier are also bonded to the liner and the wall of the root canal which actually strengthens the tooth. The tooth is retained intact and acts as a naturally occurring implant.

The means to expand or to inflate the liner by creating and maintaining positive pressure within the liner includes solids, semi-solids (gels), liquids, or gases which are biologically compatible and appropriate for dental use. Basically, all methods of expansion or inflation must create and maintain sufficient positive pressure within the liner to 1. expand or inflate the liner, 2. force the liner to conform to the shape and irregularities of the root canal wall upon intimate contact and 3. force the root canal sealer or bonding material coating the external surface of the liner throughout the dentin of the root canal. A gas or liquid can be injected into the liner for expansion or inflation while a solid or semi-solid material can be condensed into the liner to create positive pressure. The choice of the means of expansion or inflation is flexible since a variety of materials can be used depending upon the particular circumstances and physical condition of the root canal to be treated. This allows the best possible means to be employed. For example, materials which may be used include air, gutta percha, zinc oxide, aluminum oxide, silica gels, silicates, magnesium carbonates, light curable polymers, dental amalgam and the like.

In a typical embodiment, according to the present invention, the liner element (19) of the device is selected from the materials described above such as foamable polymer. The foamable polymer is encased in Teflon TM forming a conical liner (19). This two component liner is coated on its external surface (20) with root canal sealer (18) such as zinc oxide-eugenol mixture, epoxy resin or polyvinyl resin. The liner is inserted into an appropriately prepared root canal by the substrate (22) such as a plugger. The plugger (22) carries the liner (19) to the apical seat of the root canal (17) where it is plugged tightly into place. Upon removal of the plugger (22), the void or vault (23) formed is filled with cold gutta percha cones. The action of compressing the gutta percha cones into the vault (23) creates positive pressure within the liner (19) causing the Teflon TM and foamable polymer to expand. As the liner (19) is forced against the wall of the primary root canal (24) it conforms to the contours of the canal wall. Root canal sealer (18) is simultaneously applied to the primary root canal wall (24) and forced out of the associated lateral canals (13) to achieve a thorough application of sealer to the dentin (14) of the tooth.

Another embodiment, according to the invention, comprises the liner (19) with light curing bonding material (18) coating its external surface (20) and a fiber optic curing plugger (22) for insertion. The liner (19) comprises an outer wall of elastomer, such as silicone, encasing uncured composite material. The liner (19) is conical and slightly oversized. As it is plugged into an appropriately prepared root canal by the light curing plugger (22), the liner (19) is compressed and positive pressure is created within the liner vault (23). The expansion of the liner (19) expresses the light curing bonding material (18) throughout the root canal cavity, coating the wall of the primary canal (24) and filling the associated lateral canals (13). The light curing plugger (22) is then used to cure the bonding material (18) coating the external surface of the liner, and also the composite material of the liner. The plugger (22) can then be removed after curing, in which case the subsequent void or vault (23) formed can be filled with conventional filler material, such as gutta percha. Should the plugger (22) be left in place within the liner (19), the result is a bond between the tooth and the liner (19) and the plugger (22) which now acts as a core. This laminate of tooth wall, liner and core internally supports the tooth, allowing the tooth to be strengthened and act as a natural implant.

What is claimed is:

1. A device for filling and sealing a root canal of a tooth comprising
   a. a liner of nonrigid, flexible, expandable material which will conform to the contours of a root canal wall upon insertion and which will form a continuous surface with said wall and having a coating of a sealer or bonding material on its external surface which will adhere to the dentin of the root canal system;
   b. means for inserting said liner into the root canal; and
   c. means to expand or to inflate said liner.

2. A device according to claim 1 wherein the liner is a biologically compatible plastic.

3. A device according to claim 1 wherein the liner is a polyurethane material.

4. A device according to claim 1 wherein the liner is a polyethylene material.

5. A device according to claim 1 wherein the liner is PTFE.

6. A device according to claim 1 wherein the liner is a silicone elastomer.

7. A device according to claim 1 wherein the liner is foamable polymer encased in silicone elastomer.

8. A device according to claim 1 wherein the liner is foamable polymer encased in PTFE.

9. A device according to claim 1 wherein the liner is visible light curing composite encased in silicone elastomer.

10. A device according to claim 1 wherein the liner is metallic foil.

11. A device according to claim 1 wherein an interstitial liner is a foamable polymer infused with supplemental sealer or bonding material.

12. A device according to claim 1 wherein an interstitial liner is a plastic fabrication infused with supplemental sealer or bonding material.

13. A device according to claim 1 wherein an interstitial liner is a metallic fabrication infused with supplemental sealer or bonding material.

14. A device according to claim 1 wherein the means to expand or to inflate said liner according to claim 1 comprise a member selected from the group consisting of gutta percha, zinc oxide, aluminum oxide, silica gels, silicates, magnesium carbonates, light curable polymers and dental amalgam.

15. A device according to claim 1 wherein said liner is inserted into the root canal by a substrate.

16. A device according to claim 15 wherein the substrate is a plugger.

17. A device according to claim 15 wherein the substrate is a carrier.

18. A device according to claim 15 wherein the substrate is a spreader.

19. A device according to claim 15 wherein the substrate is fiber optic.

20. A device according to claim 1 wherein the means to expand or to inflate said liner according to claim 1 comprises air.

21. A device according to claim 1 wherein the liner is formed from a sheet of PTFE.

22. A method of filling and sealing a root canal of a tooth comprising, in combination, the steps of:
   a. inserting into a root canal, which has been appropriately prepared for endodontic treatment, a device (as described in claim 1 comprising a) a liner of non-rigid, flexible, expandable material which will conform to the contour of a root canal wall upon insertion and which will form a continuous surface with said wall having a coating of a sealer or bonding material on its external surface which will adhere to the dentin of the root canal system; b) means for inserting said liner into the root canal; and c) means to expand or to inflate said liner;
   b. cementing said device to the apical seat of the root canal;
   c. expanding or inflating the liner element of said device by creating and maintaining constant positive pressure within said liner to enable the external wall surface of said liner to meet and conform to the contours of the root canal wall and form an intimate and continuous interface; and
   d. simultaneously applying by said means of expansion or inflation sealer or bonding material which coats the external surface of said liner to the dentin of a root canal.

* * * * *